United States Patent

Tsujihara et al.

Patent Number: 4,886,894
Date of Patent: Dec. 12, 1989

[54] NOVEL ORGANIC PLATINUM COMPLEX AND PROCESS FOR THE PREPARATION THEREOF

[75] Inventors: Kenji Tsujihara, Urawa; Yoshihisa Arai, Funabashi; Osamu Ohtsuki, Nagaokakyo; Tadashi Nakatani, Takatsuki, all of Japan

[73] Assignee: Tanabe Seivaku Co., Ltd., Osaka, Japan

[21] Appl. No.: 164,489

[22] Filed: Mar. 4, 1988

[30] Foreign Application Priority Data

Mar. 6, 1987 [JP] Japan .................. 62-52823

[51] Int. Cl.$^4$ .......... C07F 7/28; A61K 31/28
[52] U.S. Cl. .................. 556/40; 556/137; 548/403
[58] Field of Search .......... 514/492; 556/137, 40; 548/403

[56] References Cited

U.S. PATENT DOCUMENTS

| | | |
|---|---|---|
| 4,115,418 | 9/1978 | Gale et al. |
| 4,551,502 | 11/1985 | Howell et al. ............... 556/137 |
| 4,594,238 | 6/1986 | Berch |
| 4,614,811 | 9/1986 | Gandolfi |
| 4,665,210 | 5/1987 | Ditha et al. |

FOREIGN PATENT DOCUMENTS

| | | |
|---|---|---|
| 26813 | 4/1981 | European Pat. Off. |
| 0111388 | 6/1984 | European Pat. Off. |
| WO87/02364 | 4/1987 | PCT Int'l Appl. |

OTHER PUBLICATIONS

Patent Abstracts of Japan, vo. II: No. 101.

Primary Examiner—John Doll
Assistant Examiner—Stuart L. Hendrickson
Attorney, Agent, or Firm—Birch, Stewart, Kolasch & Birch

[57] ABSTRACT

Novel organic platinum complex of the formula:

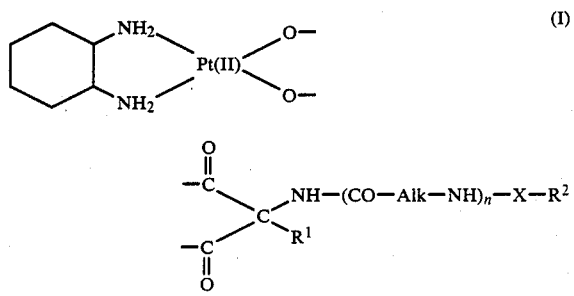

wherein $R^1$ is hydrogen atom or a lower alkyl group; $R^2$ is hydrogen atom, a substituted or unsubstituted lower alkyl group, a lower alkenyl group, a lower alkynyl agroup, a lower alkoxy group, a lower alkanoyl group, amino group, a substituted or unsubstituted nitrogen-containing hetero-monocyclic group, or an oxygen-containing hetero-monocyclic group, Alk is a lower alkylene group, X is carbonyl or sulfonyl group, n is 1 or 2, which has excellent anti-tumor activity against various tumors and is useful as an anti-tumor agent, and a process for the preparation thereof, and a pharmaceutical composition containing said compound.

5 Claims, No Drawings

NOVEL ORGANIC PLATINUM COMPLEX AND PROCESS FOR THE PREPARATION THEREOF

This invention relates to a novel organic platinum complex and a process for the preparation thereof. More particularly, it relates to a novel organic platinum complex of the formula:

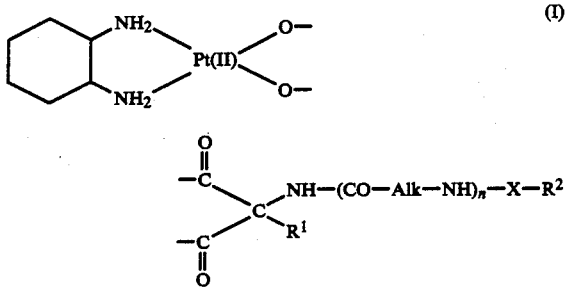

wherein
$R_1$ is hydrogen atom or a lower alkyl group,
$R_2$ is hydrogen atom, a substituted or unsubstituted lower alkyl group, a lower alkenyl group, a lower alkynyl group, a lower alkoxy group, a lower alkanoyl group, amino group, a substituted or unsubstituted nitrogen-containing hetero-monocyclic group, or an oxygen-containing hetero-monocyclic group,
Alk is a lower alkylene group,
X is carbonyl group or sulfonyl group,
n is 1 or 2,
and a process for the preparation thereof.

The organic platinum complex of this invention has an excellent anti-tumor activity and is useful as an anti-tumor agent.

Technical Background

Since it has been found that cisplatin [chemical name: cis-dichlorodiammine platinum (II)] has an anti-tumor activity [cf. Nature, Vol. 222, page 385 (1969)], there have been prepared many organic platinum complexes wherein various diamines are used as a ligand, and the anti-tumor activity of these compounds have also been studied. However, it is known that these platinum complexes have toxicity to kidney and the organ of hearing [cf. Cancer and Chemotherapy, Vol. 3, page 133 (1981)]. Besides, it is also pointed out that the known organic platinum complexes have less solubility in water and hence are hardly prepared in pharmaceutical preparations for oral or parenteral administration, and further that they are less easily transferred into organs in vivo [cf. Science, Vol. 192, page 774 (1976)].

Accordingly, it has been desired to find novel organic platinum complex having excellent anti-tumor activity with less toxicity and with high water solubility.

Summary Description of the Invention

An object of the invention is to provide a novel organic platinum complex which has excellent anti-tumor activity against various tumors with less toxicity and with high water solubility. Another object of the invention is to provide a process for the preparation of the organic platinum complex. A further object of the invention is to provide a pharmaceutical composition containing as an active ingredient said organic platinum complex which is useful as an anti-tumor agent. These and other objects and advantages of the invention will be apparent to those skilled in the art from the following description.

Detailed Description of the Invention

The organic platinum complex of this invention has the formula (I) as set forth hereinbefore. The organic platinum complex is novel and has excellent anti-tumor activity against various tumors, such as sarcoma 180, Ehrlich carcinoma, leukemia L1210, P388, Yoshida sarcoma, and ascites hepatoma, and the like, and hence, it is useful to prolong the survival time of warm-blood animals, including human, afflicted with tumors, and/or minimize the growth of tumor cells in said animals.

The organic platinum complex of this invention also has advantageous properties such as less toxicity to kidney and remarkably higher water solubility in comparison with known organic platinum complex. For instance, [2-[N-(N-formylglycyl)amino]malonato](-trans-l-1,2-diaminocyclohexane)platinum (II), when administered to mice at a dose providing 100% increase in the life span in L1210 tumor system, showed no influences on the renal function in terms of creatinine and blood urea nitrogen and said platinum complex also has 20 times higher water solubility than that of cisplatin.

Examples of the organic platinum complex of this invention include those of the formula (I) wherein $R^1$ is hydrogen atom or a lower alkyl group; $R^2$ is (i) hydrogen atom, (ii) a lower alkyl group optionally having one or two substituent(s) selected from the group consisting of hydroxy group, a lower alkoxy group, a lower alkylsulfinyl group, a lower alkylsulfonyl group, a lower alkanoyl group, a lower alkoxy-lower alkyloxy group, a halogen atom, a 5- or 6-membered nitrogen-containing hetero-monocyclic group-substituted carbonyl group (e.g. morpholinocarbonyl group), and a 5- or 6-membered oxygen-containing hetero-monocyclic group-substituted oxy group (e.g. tetrahydropyranyloxy group), (iii) a lower alkenyl group, (iv) a lower alkynyl group, (v) a lower alkoxy group, (vi) a lower alkanoyl group, (vii) amino group, (viii) a 5- or 6-membered nitrogen-containing hetero-monocyclic group optionally having a substituent selected from oxo group, a lower alkanoyl group, a lower alkoxy-lower alkanoyl group, a 5- or 6-membered oxygen-containing hetero-monocyclic group-substituted carbonyl group [e.g. oxopyrrolidinyl group, an N-(lower alkanoyl)pyrrolidinyl group, an N-(lower alkoxy-lower alkanoyl)pyrrolidinyl group, tetrahydrofurylcarbonylpyrrolidinyl group], or (ix) a 5- or 6-membered oxygen-containing hetero-monocyclic group (e.g. furyl group, tetrahydrofuryl group); X is carbonyl or sulfonyl group; and n is 1 or 2.

Among them, preferred subgenus includes the platinum complex (I) wherein $R^1$ is hydrogen atom, $R^2$ is hydrogen atom, a lower alkoxy-lower alkyl group, a lower alkylsulfonyl-lower alkyl group, a halogeno-lower alkyl group, amino group, or oxopyrrolidyl group, Alk is a lower alkylene group, X is carbonyl or sulfonyl group, and n is 1 or 2.

Most preferred subgenus includes the platinum complex (I) wherein $R^1$ is hydrogen atom, $R^2$ is hydrogen atom or a chloro-lower alkyl group, Alk is a lower alkylene group, X is carbonyl group, and n is 1 or 2.

In the platinum complex (I) of this invention, the terms "lower alkyl group", "lower alkoxy group" and "lower alkylene group" should be interpereted as referring to those of one to 6 carbon atoms, the terms "lower alkenyl group", "lower alkynyl group" and "lower alkanoyl group" should be interpreted as referring to those of 2 to 6 carbon atoms; but alkyl groups, alkoxy groups and alkylene groups of 1 to 3 carbon atoms, alkenyl groups, alkynyl groups and alkanoyl groups of 2 or 3 carbon atoms are usually exemplified as preferred examples of these groups.

In the organic platinum complex (I) of this invention, the one ligand 1,2-diaminocyclohexane has asymmetric carbons at 1- and 2-positions, and hence, there are three isomers [i.e. trans-l, trans-d, and cis-isomer (mesoform)]. The organic platinum complex of this invention includes the complex wherein these isomers, preferably trans-isomers, more preferably trans-l, are used as a ligand. Besides, in the organic platinum complex of this invention, another ligand 2-(substituted amino)-malonato ion has an asymmetric carbon at 2-position, and hence, there are two optical isomers, and furthermore, owing to the asymmetric carbon in Alk and/or $R^2$ groups and sulfinyl, there may be another optical isomer. The organic platinum complex of this invention includes also these complexes wherein any one of the isomers is used as a ligand or a mixture thereof.

The organic platinum complex of this invention can be prepared by reacting a 1,2-diaminocyclohexane platinum complex of the formula:

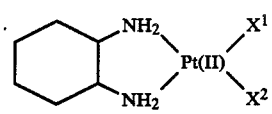

wherein $X^1$ and $X^2$ are a reactive residue, with a 2-(substituted amino)malonic acid of the formula:

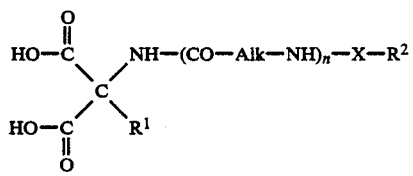

wherein $R^1$, $R^2$, Alk, X and n are as defined above, or a salt thereof.

The 1,2-diaminocyclohexane platinum complex includes the compounds of the formula (II) wherein $X^1$ and $X^2$ are each, for example, nitrato, hydroxo, a halogeno (e.g. fluoro, chloro, bromo, iodo), or are combined together to form sulfato group.

The reaction of the 1,2-diaminocyclohexane platinum complex (II) and the 2-(substituted amino)malonic acid (III) or a salt thereof can be carried out in water or an aqueous organic solvent (e.g. aqueous alkanol, aqueous acetone, etc.). For instance, in case of 1,2-diaminocyclohexane platinum complex (II) wherein $X^1$ and $X^2$ are each nitrato or are combined together to form sulfato group, it is preferably reacted with an alkali metal salt (e.g. sodium or potassium salt) of the 2-(substituted amino)malonic acid (III). In case of the platinum complex (II) wherein $X^1$ and $X^2$ are each hydroxo, it is preferably reacted with a free 2(substituted amino)malonic acid (III). These reactions proceed preferably at 20° to 40° C. Besides, in case of the 1,2-diaminocyclohexane platinum complex (II) wherein $X^1$ and $X^2$ are each halogeno, it is preferably reacted with a silver salt of 2-(substituted amino)malonic acid (III) at room temperature under light-protection.

The starting material (III) used in the above reaction is a novel compound and can be prepared, for example, by reacting an amine compound of the formula:

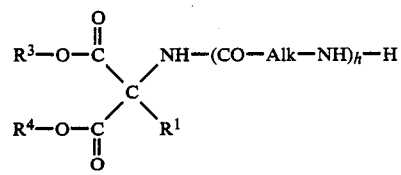

wherein $R^1$ and Alk are as defined above, $R^3$ and $R^4$ are the same or different and are each hydrogen atom or an ester residue, and h is an integer not over n such as 0, 1 or 2, or a salt thereof with an acid compound of the formula:

wherein X, $R^2$, Alk, n and h are as defined above, in the presence of a dehydrating agent, or alternatively by reacting an amine compound (IV) with a reactive derivative (e.g. an acid chloride) of an acid compound (V) in the presence of an acid scavenger, to give a compound of the formula:

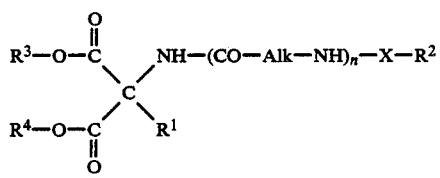

wherein $R^1$, $R^2$, X, $R^3$, $R^4$, Alk, and n are as defined above, and in case of $R^3$ and/or $R^4$ being an ester residue (e.g. a lower alkyl), followed by hydrolysis of the compound (VI) in a usual manner.

Among the starting materials, the compound of the formula (III) wherein $R^2$ is amino and X is carbonyl may also be prepared by reacting an amine compound (IV) with an isocyanate, and the compound of the formula (III) wherein $R^2$ is a lower alkyl substituted by tetrahydropyranyloxy may also be prepared by reacting a compound of the formula (III) wherein $R^2$ is a hydroxy-substituted lower alkyl with dihydropyran in the presence of an acid, optionally followed by hydrolysis of the product. Moreover, the compound of the formula (III) wherein $R^2$ is a lower alkyl substituted by a lower alkylsulfinyl or a lower alkylsulfonyl and X is carbonyl may also be prepared by reacting an amine compound (IV) with a lower alkylsulfenyl-substituted lower fatty acid, followed by oxidation of the reaction product. Further, the starting compound (III) wherein $R^1$ is a lower alkyl group may be prepared by introducing a lower alkyl group at 2-position of the starting compound (III) wherein $R^1$ is hydrogen atom, according to a conventional method of malonic ester synthesis, if required, followed by hydrolysis of the product.

The starting material (III) or a salt thereof thus prepared can be used in the reaction with 1,2-diaminocyclohexane platinum complex (II) without isolation or after being isolated.

The organic platinum complex (I) of this invention has excellent anti-tumor activity, and hence, is useful for the treatment of various tumors, such as prostate tumor, orchis tumor, ovary tumor, malignant lymphoma, leukemia, breast cancer, and the like.

The organic platinum complex (I) of this invention is highly soluble in water and can be administered by oral or parenteral route, preferably by parenteral route. The organic platinum complex (I) of this invention can be used for pharmaceutical use in the form of a pharmaceutical preparation suitable for either oral or parenteral administration. The pharmaceutical preparation includes solid preparations such as tablets, capsules, and the like, and liquid preparations such as solutions, suspensions, emulsions, and the like. When the organic platinum complex (I) is administered parenterally, it may be in the form of an injection or suppository, preferably an injection. The pharmaceutical preparations are prepared by a conventional method by admixing with a pharmaceutically acceptable carrier or diluent. Suitable pharmaceutically acceptable carrier or diluent includes, for example, gelatin, lactose, glucose, sodium chloride, starch, magnesium stearate, talc, vegetable oils, and the like. For injection, it is used in the form of an isotonic solution, which is prepared by admixing the compound (I) with an isotonic agent such as mannitol, sodium chloride, glucose, sorbitol, glycerol, xylitol, fructose, maltose, mannose, or the like. The pharmaceutical preparations may be sterilized and/or may contain auxiliaries such as preserving and stabilizing agents. The dose of the organic platinum complex (I) of this invention may vary depending on the administration routes, ages, weights and conditions of the hosts, the severity of the diseases, and the like, but it may usually be in the range of about 20 to 1,000 mg/m², preferably about 40 to 300 mg/m².

The present invention is illustrated by the following Examples but should not be construed to be limited thereto.

EXAMPLE 1

(1) Diethyl 2-[[N-(chloroacetyl)glycyl]amino]malonate (0.68 g) is added to 1N aqueous sodium hydroxide (4.7 ml), and the mixture is reacted at room temperature for 10 hours, and the reaction mixture is concentrated. The residue is washed with methanol to give disodium 2-[[N-(chloroacetyl)glycyl]amino]malonate (0.65 g).

IR $\nu_{Max}^{Nujol}$ (cm$^{-1}$): 3310 (broad), 1620 (broad)

(2) To a solution of dinitrato(trans-l-1,2-diaminocyclohexane)platinum (II) (0.87 g) in water (30 ml) is added an aqueous solution (5 ml) of the product in the above (1) (0.65 g), and the mixture is allowed to stand at room temperature for 5 hours. The reaction mixture is concentrated under reduced pressure and cooled. The precipitate is separated by filtration, washed with cold water and ethanol and dried to give [2-[[N-(chloroacetyl)glycyl]amino]malonato](trans-l-1,2-diaminocyclohexane)platinum (II) (0.81 g) as pale yellow crystalline powder.

M.p. >250° C.

IR $\nu_{Max}^{Nujol}$ (cm$^{-1}$): 3280, 3210, 3070, 1690, 1640

Example 2

To a solution of dinitrato(trans-l-1,2-diaminocyclohexane)platinum (II) (0.87 g) in water (30 ml) is added an aqueous solution (5 ml) of disodium 2-[(N-acetylglycyl)amino)malonate [prepared from the corresponding diethyl ester in the same manner as described in Example 1-(1)](0.60 g), and the mixture is allowed to stand at room temperature for 5 hours. The reaction mixture is adsorbed onto high porous resin HP-20 (manufactured by Mitsubishi Chemical Industries Limited). After washing the resin with water, the product is eluted with methanol-water (1:1), and the eluate is concentrated under reduced pressure, and to the residue is added ethanol-acetone (1:1). The precipitate is separated by filtration and dried to give [2[(N-acetylglycyl)amino]malonato](trans-l-1,2-diaminocyclohexane)platinum (II) (0.70 g) as pale yellow powder.

M.p. 257° C. (decomp.)

IR $\nu_{Max}^{nujol}$ (cm$^{-1}$): 3280, 3070, 1690, 1640

EXAMPLES 3 to 30

In the same manner as described in Examples 1 or 2, the corresponding starting materials are treated to give complexes as shown in Table 1.

TABLE 1

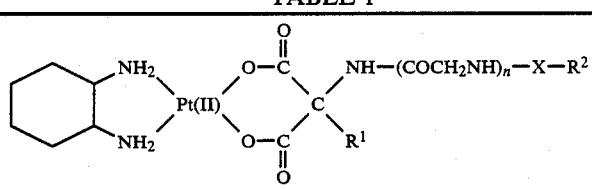

(I)

(trans-l)

(In Examples 3–28 & 30, n = 1, and in Example 29, n = 2, and in Examples 3–27, 29 & 30, X = CO, and in Example 28, X = SO$_2$, and further, in Examples 3–29, R$^1$ = H, and in Example 30, R$^1$ = CH$_3$)

| Ex. No. | Complex (I)* R² | Physical properties M.p., etc. | IR $\nu_{Max}^{Nujol}$ (cm$^{-1}$) |
|---|---|---|---|
| 3 | —H | Pale yellow powder, m.p. >250° C. | 3300, 3220, 3070, 1690, 1640 |
| 4 | —CH$_2$CH$_3$ | White powder, m.p. 240–245° C. (dec.) | 3300, 3220, 3080, 1680, 1640 |
| 5 | —CH=CH$_2$ | Pale yellow powder, m.p. >250° C. | 3460, 3260, 3100, 1670, 1640, 1610 |
| 6 | —CH$_2$OH | White powder, m.p. >250° C. | 3370, 3300, 3220, 3080, 1690, 1640 |
| 7 | —CH$_2$OCH$_3$ | White powder, m.p. 230° C. (dec.) | 3570, 3290, 3210, 3110, 3050, 1680, 1650, 1630 |
| 8 | —CH$_2$OCH$_2$CH$_3$ | White powder, m.p. 225–230° C. | 3380, 3320, 3220, 3060, 1680, 1650 |

TABLE 1-continued $$\text{(trans-l)} \quad \begin{array}{c} \text{cyclohexane-1,2-diamine-Pt(II)} \end{array} \begin{array}{c} O-C(=O) \\ O-C(=O) \end{array} C \begin{array}{c} NH-(COCH_2NH)_n-X-R^2 \\ R^1 \end{array} \quad (I)$$

(In Examples 3–28 & 30, n = 1, and in Example 29, n = 2, and in Examples 3–27, 29 & 30, X = CO, and in Example 28, X = SO$_2$, and further, in Examples 3–29, R$^1$ = H, and in Example 30, R$^1$ = CH$_3$)

| Ex. No. | Complex (I)* R$^2$ | Physical properties M.p., etc. | IR $\nu_{Max}^{Nujol}$ (cm$^{-1}$) |
|---|---|---|---|
| 9 | —CH$_2$OCH$_2$CH$_2$—OCH$_3$ | White powder, m.p. 200° C. (dec.) | 3300, 3220, 3080, 1690, 1640, 1110 |
| 10 | —OCH$_2$CH$_3$ | White powder, m.p. >250° C. | 3300, 3220, 3080, 1720, 1690, 1640 |
| 11 | —C≡CH | Pale yellow powder, m.p. >250° C. | 3220, 3080, 2100, 1680, 1640 |
| 12 | —CH$_2$COCH$_3$ | Pale yellow powder, m.p. >250° C. | 3300, 3220, 3070, 1710, 1680, 1640 |
| 13 | —NH$_2$ | White powder, m.p. >250° C. | 3350, 3220, 3080, 1680, 1640 |
| 14 | —CH$_2$SOCH$_3$ | White powder, m.p. >250° C. | 3400, 3220, 3080, 1650, 1030 |
| 15 | —CH$_2$SO$_2$CH$_3$ | White powder, m.p. >250° C. | 3370, 3270, 3210, 3130, 1690, 1670, 1640 |
| 16 | tetrahydrofuran-2-yl | White powder, m.p. 235° C. (dec.) | 3440, 3300, 3220, 3070, 1680, 1640 |
| 17 | 5-oxopyrrolidin-2-yl (l) | White powder, m.p. >250° C. | 3400, 3300, 3220, 3080, 1680, 1660, 1640 |
| 18 | —COCH$_3$ | White powder, m.p. >250° C. | 3400, 3230, 3120, 1650 |
| 19 | 1-(methoxyacetyl)pyrrolidin-2-yl (l) | White powder, m.p. 215° C. (dec.) | 3420, 3220, 3100, 1650 |
| 20 | 1-acetylpyrrolidin-2-yl (l) | White powder, m.p. 235° C. (dec.) | 3420, 3230, 3110, 1650 |
| 21 | 2,3-dihydrofuran-2-yl | White powder, m.p. >250° C. | 3300, 3220, 3070, 1680, 1640 |
| 22 | —C(OH)(CH$_3$)$_2$ | White powder, m.p. 249–251° C. (dec.) | 3400, 3200, 3120, 1650, 1620 |
| 23 | —CH(OH)CH$_3$ (l) | Pale yellow powder, m.p. 244–245° C. (dec.) | 3280, 3210, 3070, 1680, 1640 |
| 24 | —CH(OCH$_3$)$_2$ | White powder, m.p. 230° C. (dec.) | 3300, 3260, 3210, 3060, 1680, 1640 |
| 25 | —CH(OH)CH$_2$CH$_3$ | White powder, m.p. 235–236° C. (dec.) | 3300, 3210, 3060, 1680, 1640 |

TABLE 1-continued

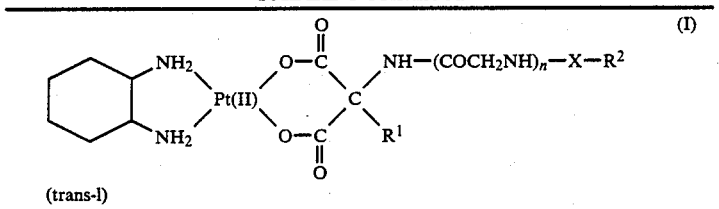

(trans-I)

(In Examples 3-28 & 30, n = 1, and in Example 29, n = 2, and in Examples 3-27, 29 & 30, X = CO, and in Example 28, X = SO$_2$, and further, in Examples 3-29, R$^1$ = H, and in Example 30, R$^1$ = CH$_3$)

| Ex. No. | Complex (I)* R$^2$ | Physical properties M.p., etc. | IR $\nu_{Max}^{Nujol}$ (cm$^{-1}$) |
|---|---|---|---|
| 26 | —CH$_2$CON(morpholino) | White powder, m.p. 240° C. (dec.) | 3310, 3220, 3070, 1690, 1640 |
| 27 | (l)-pyrrolidinyl-CO-tetrahydrofuran (dl) | White powder, m.p. 230° C. (dec.) | 3400, 3200, 3100, 1640 |
| 28 | —CH$_3$ | White powder, m.p. 240-245° C. (dec.) | 3400, 3220, 3080, 1680, 1640, 1320, 1150 |
| 29 | —CH$_2$Cl | White powder, m.p. >250° C. | 3400, 3220, 3100, 1650, 1550 |
| 30 | —H | White powder, m.p. 249-252° C. (dec.) | 3400, 3220, 3100, 1650, 1590 |

*(l) and (dl) mean stereoisomers (hereinafter, the same)

EXAMPLES 31 TO 34

In the same manner as described in Examples 1 or 2, the corresponding starting materials are treated to give the compounds as shown in Table 2.

REFERENCE 1

To a suspension of diethyl 2-aminomalonate hydrochloride (4.2 g) in tetrahydrofuran are added triethylamine (2.1 g) and N-(chloroacetyl)glycine (3.0 g), and

TABLE 2

(I-α) structure: (trans-I) Pt(II) complex with NH$_2$/NH$_2$ cyclohexane and O—C(=O)—C(H)(NHCO—Alk—NHCO—R$^2$)—C(=O)—O

| Ex. No. | Complex (I-α) Alk | R$^2$ | Physical properties M.p., etc. | IR $\nu_{Max}^{Nujol}$ (cm$^{-1}$) |
|---|---|---|---|---|
| 31 | —CH(CH$_3$)— (dl) | —CH$_3$ | Pale yellow powder, m.p. >250° C. | 3310, 3230, 3090, 1700, 1650 |
| 32 | —CH$_2$CH$_2$— | —CH$_2$OCH$_3$ | Pale yellow powder, m.p. 220-222° C. (dec) | 3280, 3220, 3070, 1690, 1640 |
| 33 | —CH$_2$CH$_2$— | tetrahydrofuran-2-yl | White powder, m.p. 225° C. (dec) | 3420, 3300, 3220, 3080, 1690, 1640 |
| 34 | —CH$_2$CH$_2$— | —CH$_2$O-tetrahydropyran | White powder, m.p. 221-223° C. (dec) | 3300, 3220, 3080, 1690, 1640 | the mixture is cooled to 0° to 5° C. To the mixture is further added N,N'-dicyclohexylcarbodiimide (4.3 g), and the mixture is stirred at the same temperature for 2 hours and then allowed to stand at room temperature overnight. Insoluble substance is filtered off from the reaction mixture, and the filtrate is concentrated under reduced pressure. To the residue is added ethyl acetate, and the insoluble substance is filtered off. The filtrate is concentrated under reduced pressure, and the residue is recrystallized from ethyl acetateisopropyl ether to give diethyl 2-[[N-(chloroacetyl)glycyl]amino]malonate (5.1 g), m.p. 104.5°–105° C.

REFERENCE EXAMPLE 2

Diethyl 2-aminomalonate hydrochloride (4.2 g), formylglycine (2.3 g) and 1-hydroxybenzotriazole (2.7 g) are dissolved in dimethylformamide (50 ml). To the solution are added N,N'-dicyclohexylcarbodiimide (4.33 g) and triethylamine (2.12 g) at 0° to 5° C. The mixture is stirred at the same temperature for 2 hours and at room temperature for 15 hours. The reaction mixture is concentrated under reduced pressure. To the residue is added ethyl acetate, and the mixture is filtered to remove insoluble materials. The filtrate is washed, dried and evaporated to remove the solvent. The residue is purified by silica gel column chromatography [solvent; chloroform-ethyl acetate (1:5)] to give diethyl 2-[(N-formylglycyl)amino]malonate (4.1 g), m.p. 95°–96° C.

REFERENCE EXAMPLES 3 to 15

In the same manner as described in Reference Example 1, the corresponding starting materials are treated to give the compounds shown in Table 3.

TABLE 3

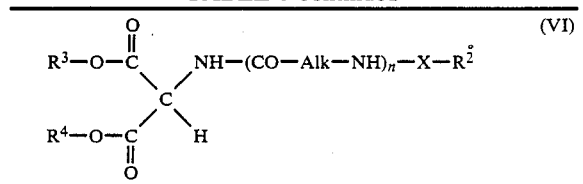

($R^3$ and $R^4$ are each ethyl, Alk is methylene, X is CO, and n is 1)

| Ref. Ex. No. | $R^2$ in the compound (VI) | Physical properties, etc. |
|---|---|---|
| 3 | —CH$_2$OH | m.p. 100–102° C. |
| 4 | —CH$_2$OCH$_3$ | m.p. 68–69° C. |
| 5 | —CH$_2$OCH$_2$CH$_3$ | m.p. 46–52° C. |
| 6 | —CH$_2$OCH$_2$CH$_2$OCH$_3$ | m.p. 67–68° C. |
| 7 | —C≡CH | m.p. 78–84° C. |
| 8 | —CH$_2$COCH$_3$ | m.p. 103–104.5° C. |
| 9 | 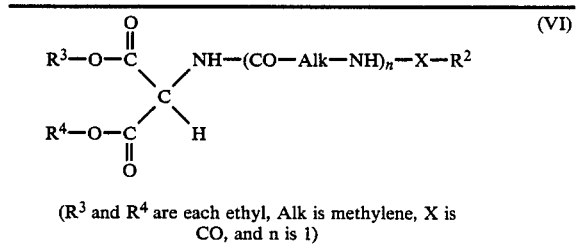 | m.p. 122–124° C. |
| 10 | —C(OH)(CH$_3$)$_2$ | m.p. 74–76° C. |
| 11 | —CH(OH)CH$_3$ (l) | m.p. 88–90° C. |
| 12 | —CH(OCH$_3$)$_2$ | m.p. 75.5–76.5° C. |
| 13 | —CH(OH)CH$_2$CH$_3$ | m.p. 68–70° C. |
| 14 | —CH$_2$CON⟨O⟩ | m.p. 125–128° C. |

TABLE 3-continued

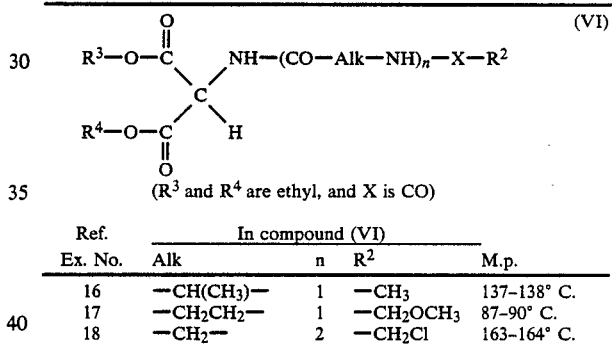

($R^3$ and $R^4$ are each ethyl, Alk is methylene, X is CO, and n is 1)

| Ref. Ex. No. | $R^2$ in the compound (VI) | Physical properties, etc. |
|---|---|---|
| 15 | (pyrrolidinyl-N-COCH$_2$OCH$_3$) (l) | m.p. 77–81° C. |

REFERENCE EXAMPLES 16 to 18

In the same manner as described in Reference Example 1-(1), the corresponding starting materials are treated to give the compounds as shown in Table 4.

TABLE 4

(VI) same structure as above ($R^3$ and $R^4$ are ethyl, and X is CO)

| Ref. Ex. No. | Alk | n | $R^2$ | M.p. |
|---|---|---|---|---|
| 16 | —CH(CH$_3$)— | 1 | —CH$_3$ | 137–138° C. |
| 17 | —CH$_2$CH$_2$— | 1 | —CH$_2$OCH$_3$ | 87–90° C. |
| 18 | —CH$_2$— | 2 | —CH$_2$Cl | 163–164° C. |

REFERENCE EXAMPLE 19

(1) To a suspension of diethyl 2-aminomalonate hydrochloride (10.6 g) in tetrahydrofuran are added N-(benzyloxycarbonyl)glycine (10.5 g) and triethylamine (5.1 g). The mixture is cooled to 0° to 5° C., and thereto is added N,N'-dicyclohexylcarbodiimide (10.8 g). The mixture is stirred at the same temperature for 2 hours and then allowed to stand at room temperature overnight. Insoluble substance is filtered off from the reaction mixture. The filtrate is distilled to remove the solvent, and to the residue is added ethyl acetate, and the insoluble substance is filtered off. The filtrate is concentrated under reduced pressure, and the residue is recrystallized from ethyl acetate-isopropyl ether to give diethyl 2-[[N-(benzyloxycarbonyl)glycyl]amino]malonate (16.0 g), m.p. 94.5°–95.5° C.

(2) To a solution of the product of the above (1) (15.8 g) in 1 % hydrochloric acid-methanol is added palladium-charcoal, and the product is reduced under atmospheric hydrogen pressure overnight. Insoluble substance is filtered off from the reaction mixture, and the filtrate is concentrated under reduced pressure. The residue is recrystallized from ethanol-isopropyl ether to give diethyl 2-(glycylamino)malonate hydrochloride (10.0 g), m.p. 97.5°–98.5° C.

(3) To a solution of the product of the above (2) (5.4 g) in methylene chloride is added triethylamine (5 g), and thereto is added dropwise propionyl chloride (2.2 g) with stirring at 0° to 5° C. The mixture is stirred at the same temperature for one hour and further at room temperature for 2 hours. The reaction mixture is washed with water, dried and then concentrated, and the residue is recrystallized from chloroform-isopropyl ether to give diethyl 2-[[N-(propionyl)glycyl]amino]malonate (4.1 g), m.p. 120°–122° C.

REFERENCE EXAMPLES 20 to 29

In the same manner as described in Reference Example 19-(3), the corresponding starting materials are treated to give the compounds shown in Table 5.

TABLE 5

$$R^3-O-C(=O)\diagdown C(H)\diagup C(=O)-O-R^4$$
$$NH-(CO-Alk-NH)_n-X-R^2$$ (VI)

($R^3$ and $R^4$ are each ethyl and n is 1, and in Reference Examples 20 to 28, X is CO, and in Reference Example 29, X is $SO_2$, and in Reference Examples 20 to 27 and 29, Alk is $-CH_2-$, and in Reference Example 28, Alk is $-CH_2CH_2-$)

| Ref. Ex. No. | $R^2$ in the compound (VI) | Physical properties, etc. |
|---|---|---|
| 20 | $-CH_3$ | m.p. 102–104° C. |
| 21 | $-CH=CH_2$ | m.p. 93–95° C. |
| 22 | $-OCH_2CH_3$ | m.p. 96–98° C. |
| 23 | $-COCH_3$ | m.p. 113–116° C. |
| 24 | tetrahydrofuran-2-yl | m.p. 103–105° C. |
| 25 | tetrahydrofuran-2-yl | m.p. 108–110° C. |
| 26 | N-acetyl-pyrrolidin-2-yl (l) | oily substance |
| 27 | N-(tetrahydrofuran-2-ylcarbonyl)pyrrolidin-2-yl (l)(dl) | m.p. 88–92° C. |
| 28 | tetrahydrofuran-2-yl | m.p. 88–90° C. |
| 29 | $-CH_3$ | m.p. 106–108° C. |

REFERENCE EXAMPLE 30

To an aqueous solution of diethyl 2-(glycylamino)malonate hydrochloride (2.7 g) is added potassium isocyanate (1.6 g), and the mixture is stirred for 10 minutes. To the reaction mixture is added acetic acid (0.7 ml), and the mixture is further stirred for 5 hours. The reaction mixture is extracted with chloroform, and the extract is concentrated under reduced pressure. The residue is recrystallized from ethyl acetate to give diethyl 2-(N-carbamoylglycyl)aminomalonate (1.58 g), m.p. 140°–141.5° C.

Reference Example 31

(1) Diethyl 2-(glycylamino)malonate and methyl-sulfenylacetic acid are treated in the same manner as described in Reference Example 1-(1) to give diethyl 2-[(N-methylsulfenylacetyl)glycylamino]malonate, m.p. 87°–88.5° C.

(2) To a solution of the product (2.64 g) obtained in the above (1) in methylene chloride is added m-chloroperbenzoic acid (2.5 g) at 0° to 5° C, and the mixture is stirred at the same temperature for 20 minutes. The reaction mixture is washed, dried and then distilled to remove the solvent. The residue is subjected to silica gel column chromatography to give diethyl 2-[(N-methylsulfinylacetyl)glycylamino]malonate (1.31 g), m.p. 127°–129° C., and diethyl 2-[(N-methylsulfonylacetyl)glycylamino]malonate (1.21 g), m.p. 178°–179.5° C.

REFERENCE EXAMPLE 32

(1) Diethyl 2-aminomalonate and N-benzyloxy-carbonyl-β-alanine are treated in the same manner as described in Reference Example 19-(1) and -(2) to give diethyl 2-[(β-alanyl)amino]malonate hydrochloride, m.p. 88°–92° C.

(2) The product of the above (1) and glycolic acid are treated in the same manner as described in Reference Example 1-(1) to give diethyl 2-[[N-(hydroxyacetyl)-βalanyl]amino]malonate, m.p. 94.5°–96° C.

(3) To a solution of the product (1.30 g) of the above (2) in methylene chloride are added dihydropyran (1.0 g) and p-toluenesulfonic acid (20 mg), and the mixture is stirred at room temperature overnight. The reaction mixture is washed, dried and then distilled to remove the solvent. The residue is purified by silica gel column chromatography to give diethyl 2-[[N-(tetrahydropyran-2-yloxyacetyl)-β-alanyl]amino]malonate (1.32 g) as viscous oil.

IR $\nu_{Max}^{Nujol}$ (cm$^{-1}$): 3300, 1755, 1740, 1660

REFERENCE EXAMPLE 33

(1) Diethyl 2-aminomalonate hydrochloride (12.7 g) and benzyloxycarbonyl chloride (11.9 g) are treated in the same manner as described in Reference Example 19-(3) to give diethyl 2-(N-benzyloxycarbonylamino)malonate (17.3 g), m.p. 36.5°–37° C.

(2) To a solution of the product of the above (1) (12.4 g) in tetrahydrofuran (100 ml) are added 63% sodium hydride oil dispersion (1.7 g). The mixture is stirred at room temperature for one hour, and methyl iodide (6.8 g) is added dropwise thereto. The mixture is further stirred at the same temperature for 20 hours and concentrated. To the residue are added water and ethyl acetate, and the organic layer is separated, dried and evaporated to remove the solvent. The resulting residue is purified by silica gel column chromatography [solvent; n-hexane-ethyl acetate (3:1)] to give oil (11.74 g). Said oil is dissolved in a mixture of ethyl acetate and methanol. To the solution is added 10% hydrochloric acid-methanol (16 ml), and the mixture is subjected to catalytic reduction using palladium-charcoal under atmospheric pressure. The reaction mixture is filtered to remove the residue and concentrated to give diethyl 2-amino-2-methylmalonate hydrochloride (7.25 g).

NMR (DMSO-$d_6$) δ:1.23 (t, 6H), 1.71 (s, 3H), 4.25 (q, 4H), 9.42 (broad s, 3H)

(3) The product of the above (2) and formylglycine are treated in the same manner as described in Reference Example 2 to give diethyl 2-[(N-formylglycyl)amino]-2methylmalonate, m.p. 98°–99° C.

What is claimed is:

1. An organic platinum complex of the formula:

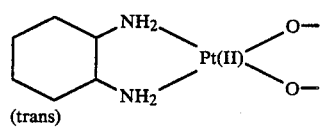
(I)

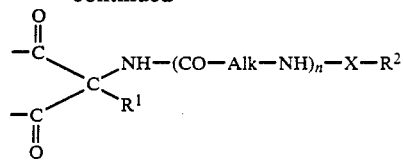
-continued wherein
$R^1$ *is a hydrogen atom*; $R_2$ is a hydrogen atom, an alkyl group having 1 to 3 carbon atoms, an alkyl group having 1 to 3 carbon atoms which has a halogen atom, an amino group, or a (tetrahydrofurylcarbonyl) pyrrolidinyl group;
Alk is an alkylene group having 1 to 3 carbon atoms;
X is carbonyl or sulfonyl group; and
n is 1.

2. The compound according to claim 1, wherein $R^2$ is a hydrogen atom or a chloro-lower alkyl group having 1 to 3 carbon atoms; X is a carbonyl group; and n is 1.

3. The compound according to claim 2, wherein $R^2$ is a hydrogen atom or chloromethyl group.

4. The compound according to claim 3, which is [2-[N-[N-(chloroacetyl)glycyl]amino]malonato](trans-1-1,2-diaminocyclohexan (II).

5. The compound according to claim 3, which is [2-[N-(N-formylglycyl)amino]malonato](trans-1-1,2-diaminocyclohexane)platin (II).

* * * * *